United States Patent
Matthews et al.

(10) Patent No.: US 9,051,800 B2
(45) Date of Patent: Jun. 9, 2015

(54) MULTI-FLUID INJECTOR CORE HOLDER

(75) Inventors: Kenneth Heidt Matthews, Kingwood, TX (US); Christopher Ray Bell, Humble, TX (US)

(73) Assignee: Halliburton Energy Services, Inc., Houston, TX (US)

(*) Notice: Subject to any disclaimer, the term of this patent is extended or adjusted under 35 U.S.C. 154(b) by 428 days.

(21) Appl. No.: 13/454,402

(22) Filed: Apr. 24, 2012

(65) Prior Publication Data

US 2013/0276554 A1 Oct. 24, 2013

(51) Int. Cl.
*E21B 25/00* (2006.01)
*G01N 15/08* (2006.01)
*E21B 49/00* (2006.01)

(52) U.S. Cl.
CPC .......... *E21B 25/005* (2013.01); *G01N 15/0806* (2013.01); *E21B 49/00* (2013.01)

(58) Field of Classification Search
CPC .................................................. G01N 15/0806
USPC ..................................... 73/38, 152.07, 152.11
See application file for complete search history.

(56) References Cited

U.S. PATENT DOCUMENTS

| | | | |
|---|---|---|---|
| 4,599,891 A | 7/1986 | Brauer et al. | |
| 4,753,107 A | 6/1988 | Reed et al. | |
| 5,263,360 A | * 11/1993 | Blauch et al. | 73/38 |
| 5,493,226 A | 2/1996 | Honarpour et al. | |
| 5,698,772 A | 12/1997 | Deruyter et al. | |

FOREIGN PATENT DOCUMENTS

WO 2013162841 A2 10/2013

OTHER PUBLICATIONS

Foreign communication from a related counterpart application—International Search Report and Written Opinion, PCT/US2013/035118, Nov. 20, 2013, 9 pages.

* cited by examiner

*Primary Examiner* — John Fitzgerald

(57) ABSTRACT

A core holder comprises a plurality of fluid flow lines, a housing, a core sleeve disposed within the housing, an end cap coupled to a first end of the core sleeve and a first end of the housing, and an injector assembly disposed within the housing and coupled to a second end of the core sleeve. The injector assembly comprises a plurality of fluid passages coupled to the plurality of fluid flow lines, and a chamber in fluid communication with the plurality of fluid passages and an interior of the sleeve.

19 Claims, 8 Drawing Sheets

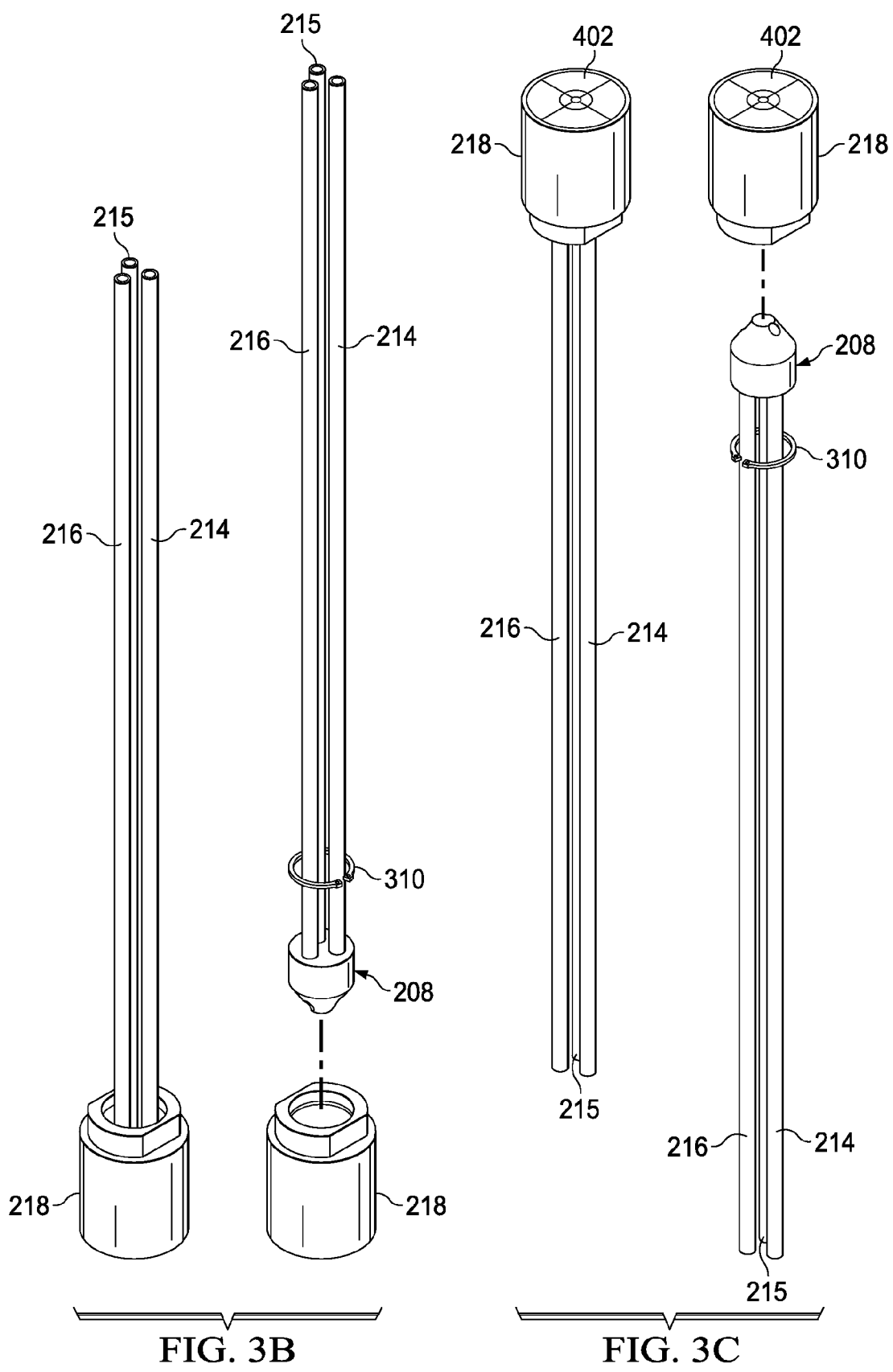

MULTI-FLUID INJECTOR CORE HOLDER

CROSS-REFERENCE TO RELATED APPLICATIONS

None.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Wellbores are sometimes drilled into subterranean formations that contain hydrocarbons to allow recovery of the hydrocarbons. The formation materials encountered while drilling into a subterranean formation can vary widely depending on the location and depth of the desired reservoir. In order to properly characterize the materials in a wellbore, one or more samples may be taken and tested to determine a variety of properties of the materials. Specific samples may be taken in various forms including cuttings from the formation in the returned drilling fluids during drilling and/or special samples cut for testing that are commonly referred to as core samples.

Core samples may be cut using core cutters to produce the core sample in a variety of diameters and lengths. The resulting core samples may then be tested in a testing apparatus to determine one or more physical properties of the sample such as the permeability, porosity, fluid flow and/or fluid and/or gas saturations in the sample. Special testing apparatuses may be used and specific methods may be carried out to determine the various properties of the samples.

SUMMARY

In an embodiment, a core holder comprises a plurality of fluid flow lines; a housing; a core sleeve disposed within the housing; an end cap coupled to a first end of the core sleeve and a first end of the housing; and an injector assembly disposed within the housing and coupled to a second end of the core sleeve. The injector assembly comprises a plurality of fluid passages coupled to the plurality of fluid flow lines; and a chamber in fluid communication with the plurality of fluid passages and an interior of the sleeve. The core holder may also include an annular region defined between an inner surface of the housing and an outer surface of the core sleeve, where the annular region is configured to accept a pressurized fluid. The injector assembly may also include a receiver comprising the plurality of fluid passages and a body portion, where the chamber can be defined by a surface of the receiver and a surface of the body portion. The injector assembly may also include a distributor disposed on an end of the injector assembly within the core sleeve. The core holder may also include a second end cap coupled to a second end of the housing. A ratio of a first distance between an outer surface of the second end cap and the chamber and a second distance between the chamber and an adjacent surface of a core sample disposed within the core sleeve may be in the range of about 1:20 to about 20:1. The chamber may comprise one or more mixing features, and the one or more mixing features may comprise one or more surface features disposed on an inner surface of the chamber, one or more fins disposed within the chamber, a mesh fill within the chamber, a gauze fill within the chamber, one or more mixing members disposed within the chamber, or any combination thereof. The core holder may also include a check valve disposed in one or more of the plurality of flow passages. For example, the one or more of the plurality of flow passages can comprise a seat, and the check-valve can comprise a ball disposed within the one or more of the plurality of flow passages. The core holder may comprise a single axis core holder, a biaxial core holder, or a triaxial core holder.

In an embodiment, a core holder comprises a housing; an injector assembly disposed within the housing and coupled to a core sleeve disposed within the housing, wherein the injector assembly is configured to: receive a plurality of fluids through a plurality of fluid flow lines; contact the plurality of fluids to form a combined fluid; and provide a fluid pathway for the combined fluid to the interior of the core sleeve. The injector assembly may comprise a chamber in which the plurality of fluids contacts to form the combined fluid. The injector assembly may also be configured to generate a turbulent flow upon contacting the plurality of fluids to improve the mixing and form the combined fluid. The core holder may also include one or more flow valves coupled to one or more of the plurality of fluid flow lines, where the flow valves may be configured to impede flow through the one or more of the plurality of fluid flow lines in a first direction and allow flow through the one or more of the plurality of fluid flow lines in a second direction. The injector assembly may also be configured to provide the combined fluid to a core sample disposed within the core sleeve within a controlled time of the plurality of fluids being contacted to form the combined fluid.

In an embodiment, a method of testing a core sample comprises receiving a plurality of fluids within a core holder; combining the plurality of fluids within the core holder to form a combined fluid; contacting the combined fluid with a core sample within the core holder; and determining one or more properties of the core sample. The one or more properties of the core sample may comprise a permeability, a regained permeability, a porosity, a fluid flow through the core sample, a fluid saturation in the core sample, a gas saturation in the core sample, or any combination thereof. The plurality of fluids may react to form a reaction product in the combined fluid. The method may also include selecting a fluid for use in a subterranean formation based on the one or more properties of the core sample.

These and other features will be more clearly understood from the following detailed description taken in conjunction with the accompanying drawings and claims.

BRIEF DESCRIPTION OF THE DRAWINGS

For a more complete understanding of the present disclosure and the advantages thereof, reference is now made to the following brief description, taken in connection with the accompanying drawings and detailed description:

FIG. 3B illustrates an isometric view of an injector assembly according to an embodiment.

FIG. 3C illustrates another isometric view of an injector assembly according to an embodiment.

DETAILED DESCRIPTION OF THE EMBODIMENTS

Figure 1:
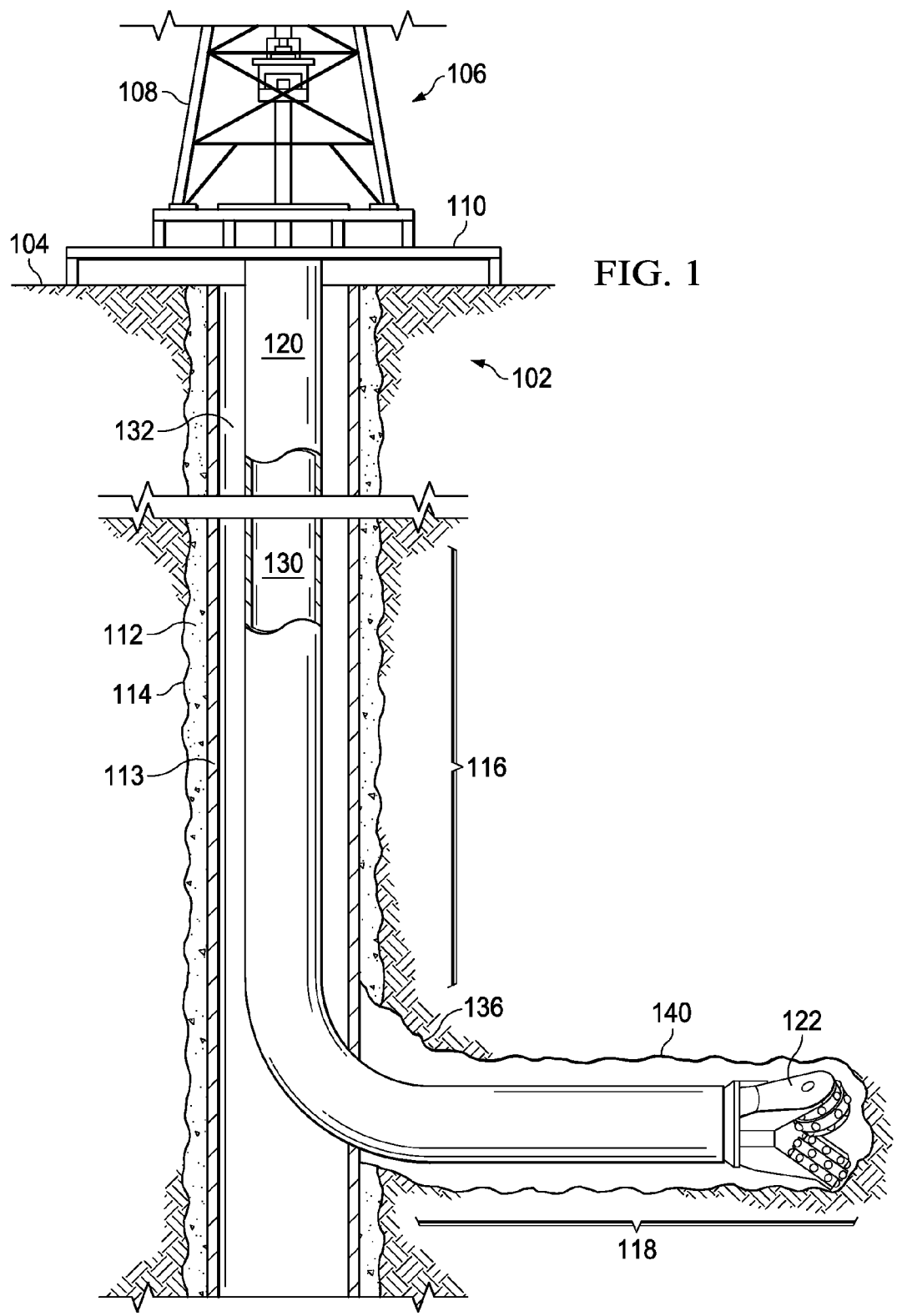
FIG. 1 illustrates a cut-away view of an embodiment of a wellbore servicing system.

In the drawings and description that follow, like parts are typically marked throughout the specification and drawings with the same reference numerals, respectively. The drawing figures are not necessarily to scale. Certain features of the invention may be shown exaggerated in scale or in somewhat schematic form and some details of conventional elements may not be shown in the interest of clarity and conciseness.

Unless otherwise specified, any use of any form of the terms "connect," "engage," "couple," "attach," or any other term describing an interaction between elements is not meant to limit the interaction to direct interaction between the elements and may also include indirect interaction between the elements described. In the following discussion and in the claims, the terms "including" and "comprising" are used in an open-ended fashion, and thus should be interpreted to mean "including, but not limited to . . . ". Reference to up or down will be made for purposes of description with "up," "upper," or "upward" meaning toward the surface of the wellbore and with "down," "lower," or "downward" meaning toward the terminal end of the well, regardless of the wellbore orientation. Reference to in or out with respect to a core holder will be made for purposes of description with "in," "inner," or "inward" meaning toward the center of the core sample holder in a radial direction (i.e., towards the central axis of the core holder) and with "out," "outer," or "outward" meaning towards the wall or outer surface of the core holder in a radial direction, regardless of the wellbore orientation. The various characteristics mentioned above, as well as other features and characteristics described in more detail below, will be readily apparent to those skilled in the art with the aid of this disclosure upon reading the following detailed description of the embodiments, and by referring to the accompanying drawings.

As described in more detail herein, a core holder comprising an injector assembly may be used to perform one or more tests on a sample. In an embodiment, the sample may comprise a core sample taken from a wellbore disposed in a subterranean formation. Alternatively, a sample of a rock that is representative of the rock in the subterranean formation may be used as a core sample. The tests performed on the core sample may be used to select one or more fluids and/or techniques for use with the subterranean formation while drilling a wellbore and/or performing a workover procedure (e.g., fracturing) during the life of a wellbore.

Referring to FIG. 1, an example of a wellbore operating environment is shown. As depicted, the operating environment comprises a drilling rig 106 that is positioned on the earth's surface 104 and extends over and around a wellbore 114 that penetrates a subterranean formation 102 for the purpose of recovering hydrocarbons. The wellbore 114 may be drilled into the subterranean formation 102 using any suitable drilling technique. The resulting wellbore 114 extends substantially vertically away from the earth's surface 104 over a vertical wellbore portion 116, deviates from vertical relative to the earth's surface 104 over a deviated wellbore portion 136, and transitions to a horizontal wellbore portion 118. In alternative operating environments, all or portions of a wellbore may be vertical, deviated at any suitable angle, horizontal, and/or curved. The wellbore may be a new wellbore, an existing wellbore, a straight wellbore, an extended reach wellbore, a sidetracked wellbore, a multilateral wellbore, and other types of wellbores for drilling and completing one or more production zones. Further the wellbore may be used for both producing wells and injection wells.

The drilling rig 106 comprises a derrick 108 with a rig floor 110 through which the drill string 120 extends downward from the drilling rig 106 into the wellbore 114. In an embodiment, the drill string 120 comprises a drill collar and is disposed within the wellbore 114. A drill bit 122 is located at the lower end of the drill string 120 and carves the wellbore 114 through the subterranean formation 102. The drill bit 122 may comprise one or more bits. The drilling rig 106 comprises a motor driven winch and other associated equipment for extending the drill string 120 into the wellbore 114 to position the drill string 120 for drilling the wellbore 114. While the operating environment depicted in FIG. 1 refers to a stationary drilling rig 106 for lowering and setting the drill string 120 within a land-based wellbore 114, in alternative embodiments, mobile workover rigs, wellbore servicing units (such as coiled tubing units), and the like may be used to lower the drill string 120 into a wellbore. It should be understood that a drill string 120 may alternatively be used in other operational environments, such as within an offshore wellbore operational environment.

In an embodiment, the drill string 120 may also comprise one or more instruments and/or instrument subs for measuring various parameters during the drilling process. Common measurements obtained during drilling may include weight-on-bit, torque-on-bit, rate-of-penetration, temperature, and/or pressure near the bit. Additional measurements may include the torque on the drill string 120, the power output of any motors and/or pumps located at the surface of the wellbore, and the like. The drill string may also include one or more logging tools for measuring one or more properties of the subterranean formation 102 and/or the drilling fluid. The measurements from any of these instruments, sensors, and/or logging tools may be used to adjust one or more drilling process parameters and/or a drilling fluid composition. In some embodiments, one or more specialized drill bits may be used to cut cores from the subterranean formation during drilling. The resulting core samples may comprise cylindrical sections of the subterranean formation that can be divided into smaller portions for testing using the core holder described herein.

In an embodiment, a drilling fluid is pumped from a storage reservoir pit near the wellhead, down an axial passageway 130, through the drill string 120, and out of apertures in the drill bit 122. As used herein, the "drilling fluid" may also be referred to as a "drilling mud." The drilling fluid is pumped from the storage pit near the well head by a pumping system comprising one or more pumps. The drilling fluid may travel through a drilling fluid supply line coupled to the central passageway 130 extending throughout the length of the drill string 120. The annular region 132 between the drill string 120 and the sidewalls of the wellbore 114 forms the return flow path for the drilling fluid. Drilling fluid is, in this manner, forced down the drill string 120 and exits into the borehole through apertures in the drill bit 122 for cooling and lubricating the drill bit and carrying the formation cuttings produced during the drilling operation back to the surface. A fluid exhaust conduit may be connected from the annular region 132 at the well head for conducting the return drilling fluid flow from the wellbore 114 to the storage pit. The drilling fluid may be handled and treated by various apparatus, comprising out gassing units and circulation tanks for maintaining a preselected mud viscosity and consistency. The cuttings produced by the drill bit 122 cutting the subterranean formation 102 may be carried with the returned drilling fluid. The cuttings may be removed at various points including the storage pit and/or a shaker designed to allow the drilling fluid to pass through while retaining the cuttings for disposal. These cuttings may be used to determine one or more characteristics of the subterranean formation. One or more rock samples comprising similar properties may then be used as a core sample in the core holder as described herein.

The embodiment shown in FIG. 1 may also be used to dispose and/or set one or more casing strings 113 within the wellbore 114 to thereby form one or more cased sections of the wellbore 114. In the embodiment shown in FIG. 1, the casing string 113 may be conveyed into the subterranean formation 102 in a conventional manner (e.g., using the same motor driven winch and other associated equipment used to extend the drill string 120 into the wellbore 114) and may subsequently be secured within the wellbore 114 by filling an annulus 112 between the casing string 113 and the wellbore 114 with cement. The drilling of the wellbore 114 may then proceed by passing the drill string 120 through the cased section of the wellbore 114. In alternative operating environments, a vertical, deviated, or horizontal wellbore portion may be drilled, cased, and cemented and/or portions of the wellbore may be left uncased. For example, uncased and drilled section 140 may comprise a section of the wellbore 114 ready for being cased with a wellbore tubular and/or ready for production.

After the wellbore 114 is completed, one or more completion operations may be performed to provide a wellbore capable of producing hydrocarbons. In addition to completion operations, one or more workover operations may be performed during the life of the wellbore 114 to alter the configuration of the wellbore, correct any problems, and/or improve the performance of the wellbore. Each of these operations may use a variety of fluids. As described in more detail herein, the results from one or more tests performed with the core holder comprising the injector assembly described herein may be used to determine a fluid for use in a drilling, completion, and/or workover operation.

Figure 2A:
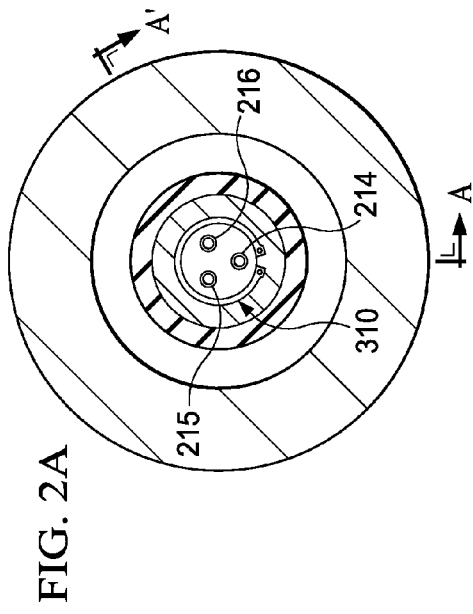
FIG. 2A illustrates a cross sectional view of a core holder accordingly to an embodiment.
Figure 2B:
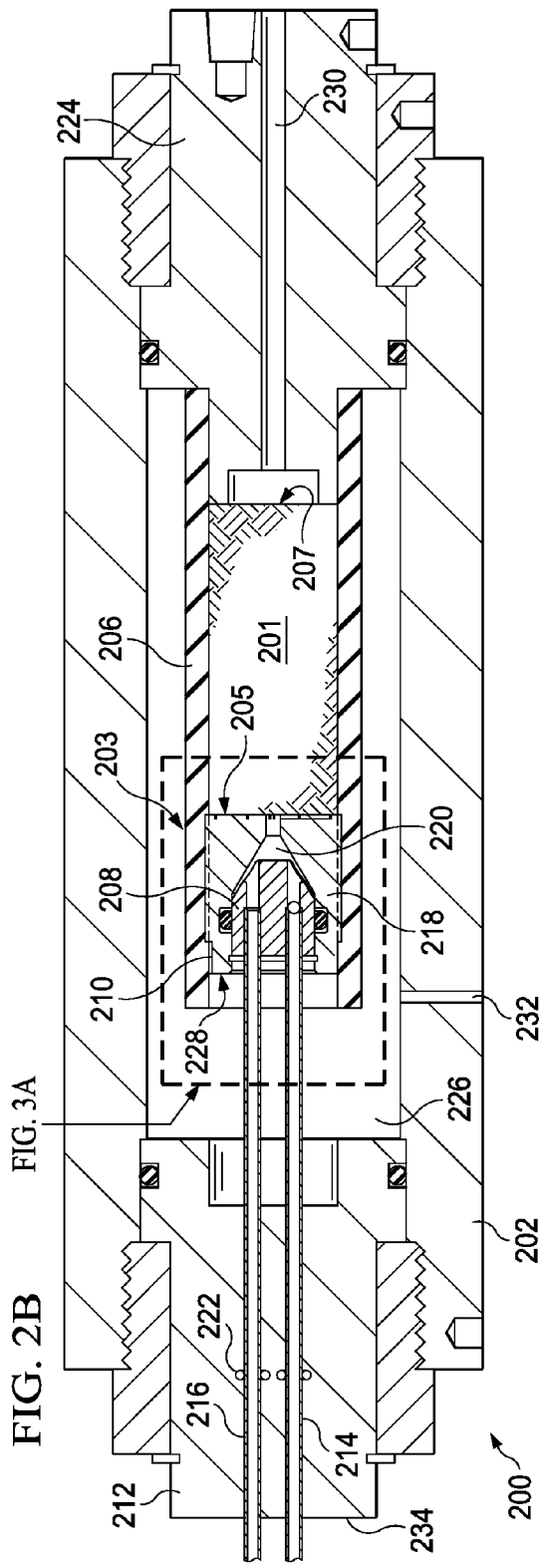
FIG. 2B illustrates a cross sectional view of a core holder taken along line A-A' of FIG. 2A accordingly to an embodiment.

FIG. 2A illustrates a cross-sectional view of a core holder 200 comprising a plurality of flow lines 214, 215, 216. FIG. 2B illustrates another cross-sectional view of the core holder 200 of FIG. 2A along the line A-A'. As shown in FIG. 2B, an embodiment of a core holder 200 generally comprises a sleeve 206 disposed about a core sample 201 and engaged with a first end cap 212 and a second end cap 224. A variety of core samples 201 can be used with the core holder 200 described herein. In general, the core sample 201 may comprise a cylindrical shape with a diameter between about 0.125 inches and 6 inches and a length between about 1 inch to about 12 inches. Each end cap 212, 224 may be engaged with a housing 202 that maintains pressure within the housing 202. The sleeve 206 may provide for a fluid tight engagement between the end caps 212, 224 within the housing 202. An annular region 226 may exist between the inner surface of the housing 202 and the outer surface of the sleeve 206 to allow for a pressurized fluid to be contained within the annular region and exert a force on the sleeve 206. The force on the sleeve 206 may be transferred through the sleeve 206 to the core sample 201 disposed within the sleeve 206. An injector assembly 203 may be disposed adjacent one end of the core sample 201 and provide a fluid to a first surface 205 of the core sample 201. The injector assembly 203 may have one or more fluid flow lines 214, 216 coupled to the injector assembly 203 for introducing and distributing the fluid across the face of the first surface 205 of the core sample 201. In use, the fluid may be pressurized and may flow through the core sample 210 to a second surface 207. A fluid outlet 230 may be in fluid communication with the second surface 207 and allow one or more properties of the fluid to be measured at the fluid outlet 230. For example, a fluid flow rate, pressure, temperature, composition, or the like can be measured at the second surface 207 and/or within the fluid outlet 230 to determine one or more properties of the core sample 201. In an embodiment, the various measurements of the core sample 201 and/or the fluid passing through the core sample 201 may be used to determine one or more properties of the fluid and/or the core sample 201 such as the permeability, regained permeability, porosity, fluid flow, fluid saturation and/or gas saturation in the core sample 201.

While the injector assembly 203 disclosed herein may assume a variety of forms, it will be appreciated that the injector assembly 203 described herein is configured to receive one or more fluids through a plurality of fluid flow lines 214, 216, mix the fluids, and contact the resulting mixed fluid with the first surface 205 of the core sample 201 within the sleeve 206 of the core holder 200. The injector assembly 203 may be disposed adjacent the first surface 205 of the core sample 201 so that a plurality of fluids can be mixed and introduced to the first surface 205 of the core sample 201 without having to travel through additional lengths of fluid lines. This configuration may allow for a plurality of fluids that react with each other to be combined and introduced to the core sample 201 prior to the completion of a chemical reaction, which may not be practical based on first combining the fluids and then introducing the fluids to the core sample 201 through a single fluid flow line.

The injector assembly 203 described herein has a plurality of fluid flow lines 214, 216 coupled to the injector assembly 203. In an embodiment illustrated in FIGS. 3A, 3B, and 3C, the injector assembly 203 comprises a receiver 208 engaged within a body portion 218. A first fluid flow line 214 and a second fluid flow line 216 may be received within the receiver 218 and form a substantially fluid tight seal with the receiver 218. The fluid flow lines 214, 216 may be coupled to one or more fluid sources and provide a fluid communication path between the one or more fluid sources and the core holder 200. In an embodiment, the fluid flow lines 214, 216 may have a length sufficient to couple the core holder 200 with the fluid sources, and in an embodiment may have a length ranging from about 0.5 feet to about 15 feet. While described herein as comprising two fluid flow lines 214, 216, the injector assembly 203 described herein may be used with any plurality of fluid flow lines. For example, the embodiment of the core holder 200 illustrated in FIG. 2A comprises three fluid flow lines, though only two are shown in the cross-section illustrated in FIG. 2B. In an embodiment, the injector assembly 203 may receive any plurality of fluid flow lines such as two fluid flow lines, three fluid flow lines, four fluid flow lines, or five or more fluid flow lines.

A first fluid passage 302 may be in fluid communication with the first fluid flow line 214 and may extend through the receiver 208. Similarly, a second fluid passage 304 may be in fluid communication with the second fluid flow line 216 and may extend through the receiver 208. The receiver 208 may comprise a first generally cylindrical section and a second generally frusto-conical section. In an embodiment, the first fluid passage 302 and/or the second fluid passage 304 may extend through the receiver 208 and exit the receiver 208 at or near the frusto-conical section. In an embodiment with more than two fluid flow lines 214, 216, a corresponding number of fluid passages may be disposed in the receiver 208 to provide fluid communication between the fluid flow lines through the receiver 208.

In an embodiment, the receiver 208 is configured to engage the body portion 218. The body portion 218 generally comprises a cylindrical outer surface that is sized to be received within the sleeve 206 adjacent the core sample 201. The sleeve 206 may form a substantially fluid tight seal with the outer surface of the body portion 218. A first section of the body portion 218 furthest from the core sample 201 may have a reduced radius relative to a second section of the body portion 218, thereby forming a shoulder 306 between the first section and the second section. The sleeve 206 may engage the outer surface of the body portion 218 including the shoulder 306 and be retained in position relative to the body portion 218 due to the interaction of the shoulder 306 with the sleeve 206.

The body portion 218 may have a fluid passageway disposed therethrough. A first section of the fluid passageway may comprise a generally cylindrical inner surface and be configured to receive the first generally cylindrical section of the receiver 208. A second section 326 of the fluid passageway may comprise a generally frusto-conical inner surface and be configured to receive the second generally frusto-conical section of the receiver 208. The receiver 208 may be prevented from passing through the fluid passageway due to the interaction of the outer surface of the generally frusto-conical section of the receiver 208 engaging the inner surface of the generally frusto-conical section 326 of the body portion 218. A third section 324 of the fluid passageway may pass through body portion 218 to provide a fluid communication path between the first and second sections of the body portion 218 and a second end of the body portion 218. The third section 324 may then be configured to be disposed adjacent to the core sample 201 and provide a fluid communication pathway to the core sample 201. In order to provide for a sealing engagement between the receiver 208 and the body portion 218, one or more seals 308 (e.g., o-ring seals) may be disposed in a recess disposed in an inner surface of the body portion 218 and/or an outer surface of the receiver 208.

Figure 3A:
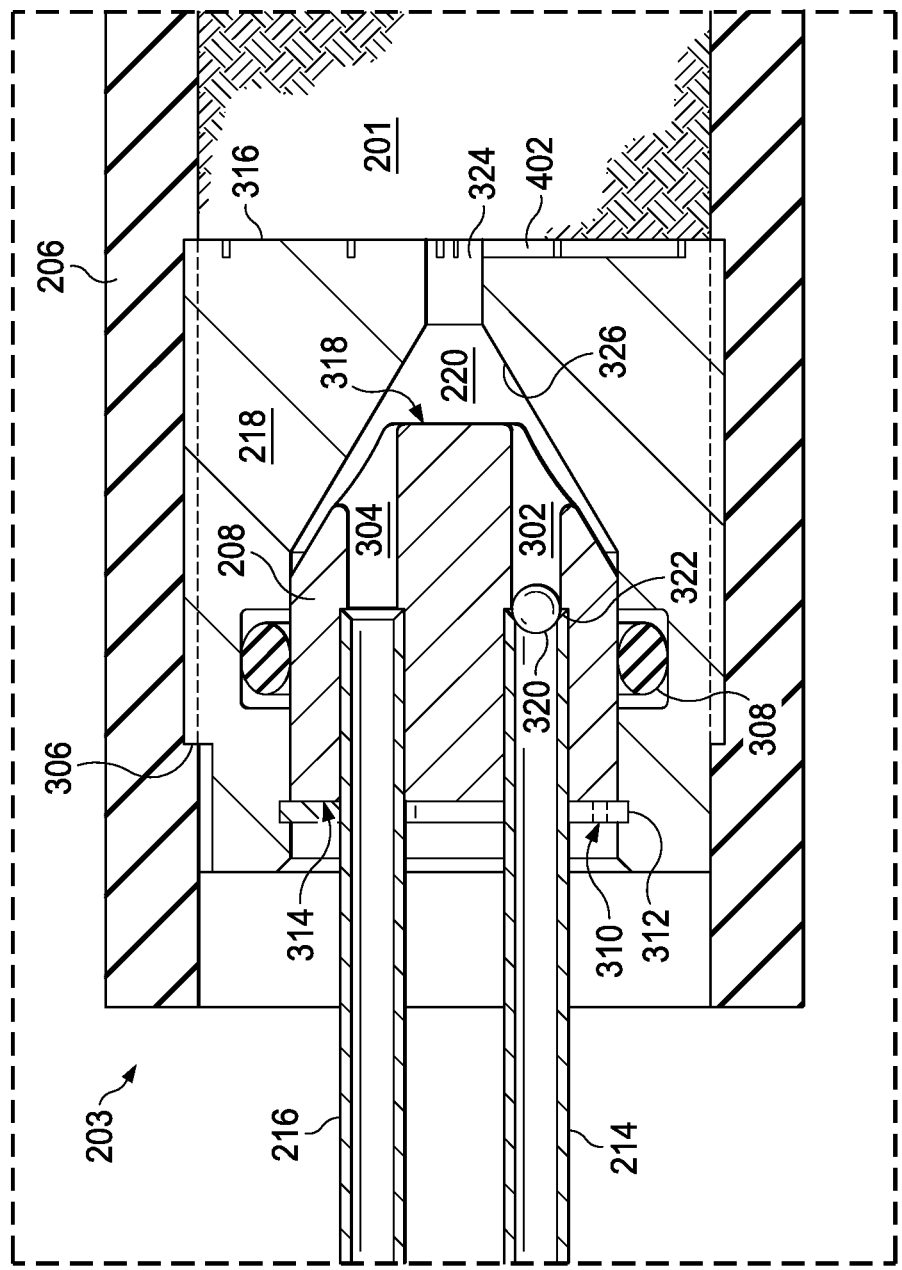
FIG. 3A illustrates a cross sectional view of an injector assembly according to an embodiment.

As shown in FIGS. 3A, 3B, and 3C, a retaining clip 310 such as a c-ring may be disposed about the fluid flow lines 214, 216 and engage a retaining clip recess 312 on the inner surface of the body portion 218. The retaining clip 310 may be sized to retain the receiver 208 within the fluid passageway by engaging a first surface 314 of the receiver 208. In an embodiment, the receiver 208 may be engaged with the body portion 218 using a variety of coupling mechanisms. For example, the receiver 208 may be threadedly coupled to the body portion 218 through an engagement between corresponding threads on the outer surface of the receiver 208 and the inner surface of the body portion 218.

A second end 316 of the body portion 218 may be configured to engage a core sample 201. In order to allow the fluid passing through the third section 324 of the fluid passageway to contact the surface of the core sample 201, the second end 316 of the body portion 218 may optionally comprise a distributor 402, as shown in FIG. 3C. In an embodiment, the distributor 402 may comprise one or more protrusions extending from the second end 316 of the body portion 218 to allow the fluid to flow out of the body portion 218 and into a space defined between the body portion 218 and the surface of the core sample 201. The distributor 402 may also comprise one or more fins and/or grooves to provide a fluid passage from the fluid outlet from the body portion 218 to the surface of the core sample 201. In an embodiment, the distributor 402 may comprise radial fins (e.g., a crosshair type pattern) and/or spiral protrusion to define a spiral channel.

When the receiver 208 is engaged with the body portion 218, a chamber 220 may be formed that is defined by a second surface 318 of the receiver 208 and the inner surface of the body portion 218. In an embodiment, the chamber 220 may be configured to provide for mixing between the fluids introduced through the plurality of fluid flow lines 214, 216. The chamber 220 may be in fluid communication with the plurality of fluid flow lines 214, 216 through an annular region between the receiver 208 and the body portion 218, and the chamber 220 may be in fluid communication with the surface of the core sample 201 through the third section 324 of the fluid passageway. When a fluid is introduced through the fluid flow lines 214, 216, the fluid may pass through the corresponding fluid passage 302, 304 and into the chamber 220. The fluid may then pass to the core sample 201 through the third section 324 of the fluid passageway. This configuration may allow the fluid mixing location within the chamber 220 to be disposed within the core holder 200. In an embodiment, the injector assembly 203 may be disposed within the core holder 200 such that the ratio of the distance between the outer surface 234 of the first end cap 212 and the chamber 220 and the distance between the chamber 220 and the surface 205 of the core sample 201 adjacent the body portion 218 (and/or the surface of the injector assembly adjacent the surface of the core sample 201) is in the range of about 1:20 to about 20:1, about 1:1 to about 20:1, or about 1:10 to about 20:1.

Figure 4A:
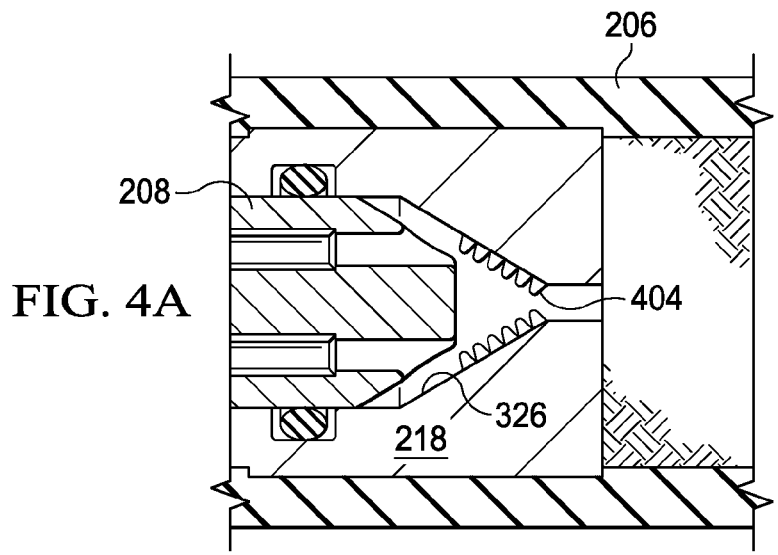
FIGS. 4A through 4G illustrate various embodiments of mixing features useful with an injector assembly according to an embodiment.
Figure 4B:
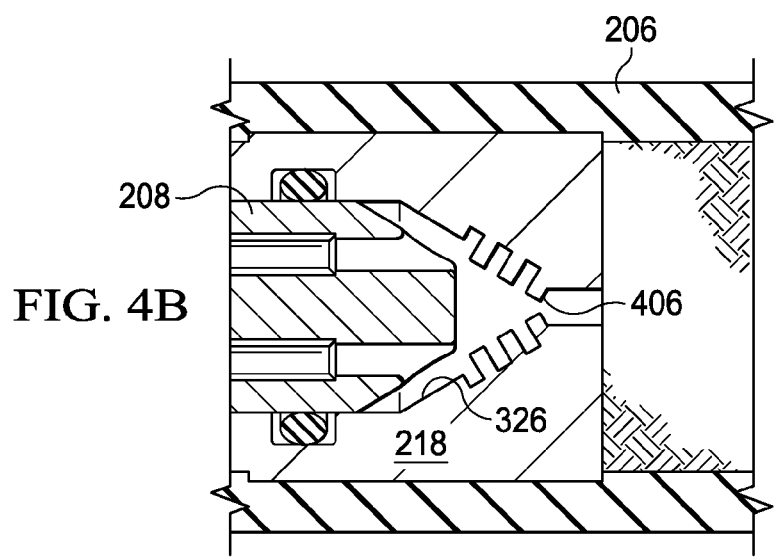
Figure 4C:
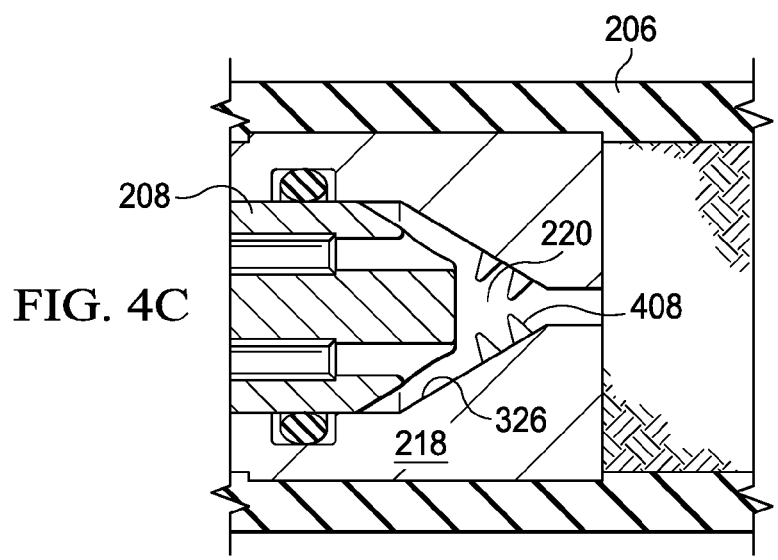
Figure 4D:
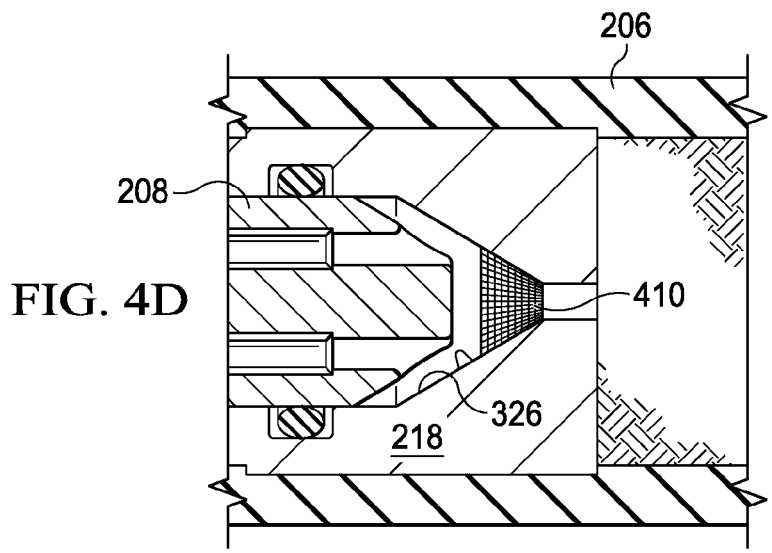

In an embodiment, the chamber 220 may optionally comprise one or more mixing features. The mixing features may be used to provide for a desired level of mixing within the chamber. The mixing features may generally be used to generate a turbulent flow within the chamber 220 and/or the third section 324 of the fluid passageway, thereby mixing a plurality of fluids to a desired degree prior to contacting the mixed fluids with the core sample 201. In an embodiment, the mixing features may include, but are not limited to, one or more surface features disposed on an inner surface of the body portion, one or more fins, swirl, and/or turbulence inducing features disposed in the chamber, a mesh or gauze type fill within the chamber, and/or one or more mixing members disposed within the chamber. As shown in FIGS. 4A and 4B, suitable surface features 404, 406 may comprise stippling, roughening, recesses, protrusions, ridges, or other turbulence inducing structures of a variety of shapes and sizes disposed on an inner surface of the body portion 218 (e.g., on an inner surface of the second section 326 of the body portion 218) and/or on an outer surface of the receiver 208 forming a portion of the chamber 220. In an embodiment shown in FIG. 4C, one or more fins or other swirl inducing structures 408 may be disposed for example, on an inner surface of the body portion 218. The fin or other swirl inducing structure 408 may be configured to provide for a turbulent flow within the chamber 220. In an embodiment shown in FIG. 4D, a mesh and/or gauze type fill 410 may be disposed within the chamber to provide a more tortuous flow path for the fluids. The tortuous flow paths may improve mixing as the fluids pass therethrough.

Figure 4E:
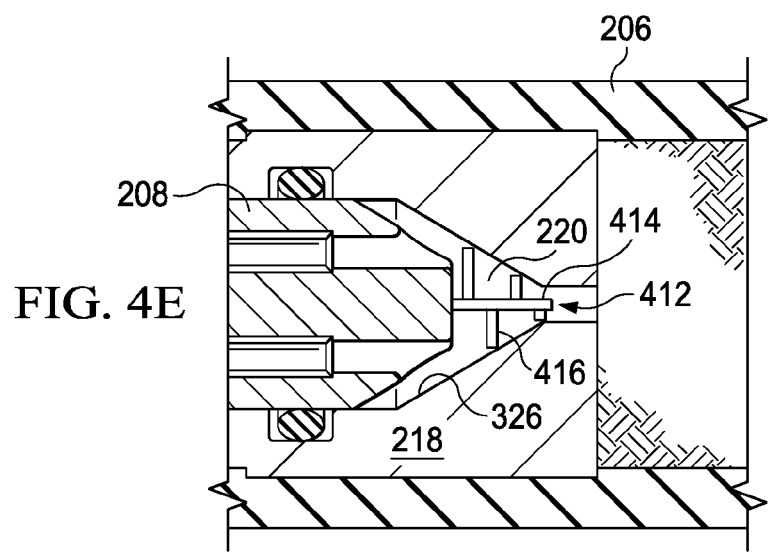
Figure 4F:
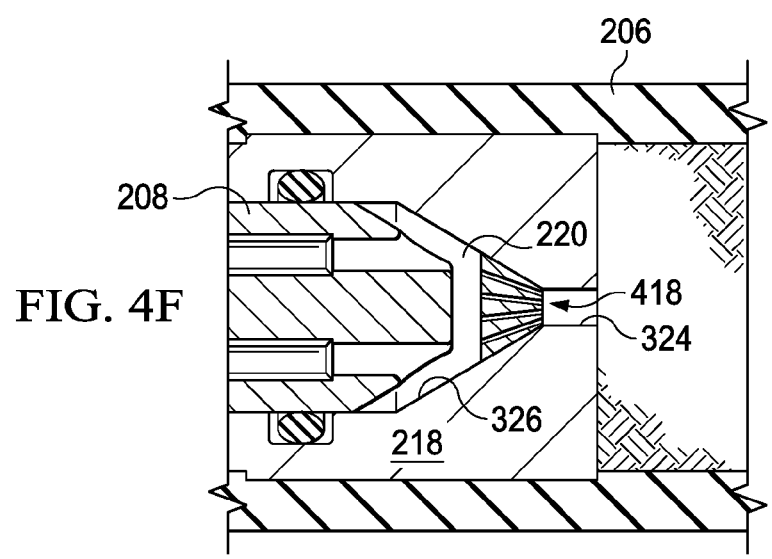
Figure 4G:
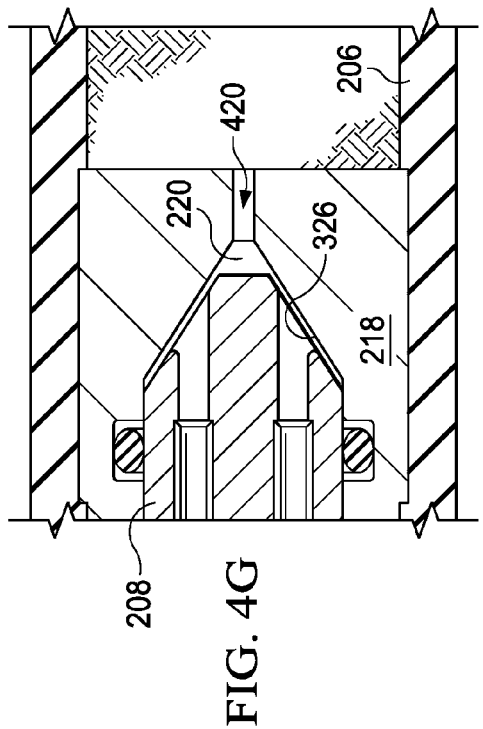

Suitable mixing members may comprise one or more mechanisms or structures configured to lengthen the flow path of the fluid and/or reduce the diameter of the flow path within the chamber. In an embodiment shown in FIG. 4E, a helical flow insert 412 comprising a central column 414 and a fin 416 arranged in a helical pattern about the central column 414 could be disposed within the chamber 220. The insert 412 may be configured to engage the inner surface of the body portion 218 and provide a helical flow path for the fluids between the fin 416. The increased length of the flow path may provide additional mixing along its length. In an embodiment shown in FIG. 4F, a plurality of small diameter flow tubes 418 may be disposed within the chamber 220. The tubes 418 may be configured to receive the fluids and force the flow of the fluids through the plurality of tubes 418 before being passed to the third section 324 of the fluid passageway. The reduced flow diameter may provide an increased turbulence to improve mixing. In still another embodiment as shown in FIG. 4G, a nozzle structure 420 may be disposed in the chamber 220 and the fluid flow may be directed through the nozzle structure 420. The fluids may be sheared in a reduced fluid passageway within the nozzle structure 420, thereby providing for improved mixing within the chamber 220. In an embodiment, the nozzle structure 420 may be created by the end of the receiver 208 forming a relatively narrow flow path with the body portion 218. As the fluid flows through the narrow space, the fluid may be sheared and improve mixing.

In an embodiment, the mixing feature may comprise an orientation of the fluid passages in communication with the chamber 220 arranged to generate a swirling fluid flow and/or a turbulent flow within the chamber 220. For example, one or more of the fluid passages 302, 304 may be disposed at a non-parallel angle to the longitudinal axis of the core holder 200. A fluid entering the chamber 220 at a non-parallel angle may then generate a swirling flow within the chamber 220, which may improve the mixing between a plurality of fluids introduced into the chamber 220. The use of a non-parallel orientation of the fluid passages 302, 304 may be used alone or in combination with any of the other mixing features described above.

Returning to FIGS. 3A, 3B, and 3C, one or more flow valves may be optionally used with the injector assembly 203 to regulate the flow and/or flow direction through one or more of the fluid flow lines 214, 216. When a plurality of fluid flow lines 214, 216 are coupled to the injector assembly 203, the injection of a fluid through one of the fluid flow lines 214, 216 at a pressure above a pressure within another fluid flow line may result in backflow of the fluid through the other fluid flow line. In order to protect against unintentional backflow and/or provide for the use of a single fluid flow line to provide a fluid to the core sample 201, a flow valve may be used with one or more of the fluid flow lines 214, 216. In an embodiment, the flow valve may comprise a check-valve disposed within the injector assembly 203 to allow flow from a fluid flow line 214 to the core sample 201 while preventing flow from the core sample 201, chamber 220, and/or any other fluid flow line 216 into the fluid flow line 214. In an embodiment, each fluid flow line 214, 216 may comprise a flow valve. Alternatively, only one fluid flow line or less than all of the fluid flow lines may comprise a flow valve. In an embodiment, one of the plurality of fluid flow lines may not comprise a flow valve. This may allow for a return flow from the core sample 201 through the fluid flow line for tests involving two directional flow through the core sample 201.

In an embodiment shown in FIG. 3A, the check-valve may comprise a ball 320 disposed within one or more of the fluid passages 302, 304. The ball 320 may be retained within the fluid passage 302 by a seat 322 disposed within the fluid passage 302 between the ball 320 and the fluid flow line 214. On the other side of the ball 320, the annular space between the receiver 208 and the body portion 218 may be configured to have a clearance less than the diameter of the ball 320, thereby retaining the ball 320 with the fluid passage 302. When a fluid is passed from the fluid flow line 214 towards the core sample 201, the ball 302 may be displaced towards the body portion 218. When engaged with the body portion 218, sufficient flow paths may be formed between the ball 320, the body portion 218, and/or the receiver 208 to allow the fluid to pass into the chamber 220. When a fluid is passed from the direction of the core sample 201 towards the fluid flow line 214, the ball 320 may be carried into contact with the seat 322, thereby providing a substantially fluid tight seal against fluid passing into the fluid flow line 214. While illustrated as having a ball only in the fluid passage 302, a similar ball 320 and seat 322 can be disposed in one or more additional fluid passages such as fluid passage 304. While illustrated as being disposed within the injector assembly 203, it should be understood that a flow valve may also be disposed within the fluid flow lines 214, 216 outside of the injector assembly 203 to achieve the same flow protection benefits.

The core holder 200 described herein may be used to provide a mixed and/or combined fluid in the chamber 220 adjacent the core sample 201. Various fluids may be combined to initiate a chemical reaction and produce a reaction product. Some of these fluids may react faster than the mixed fluid can travel through the fluid flow lines 214, 216 and into the core sample 201. By separately introducing the fluids through the plurality of fluid flow lines 214, 216 and combining the fluids in the chamber 220, the mixed fluid may be introduced to the core sample 201 prior to the reaction achieving a certain degree of completion. For example, a two component epoxy may initiate a hardening reaction upon mixing of a first and second fluid. When a two component epoxy is combined and then introduced into a single fluid flow line, the epoxy may harden before being introduced into the core sample 201 and/or a portion of the epoxy may harden in the fluid flow line, thereby clogging the fluid flow line. When at least two lines are used with the two component epoxy, the two fluids may be combined and mixed within the chamber 220 and the combined mixture may be introduced to the core sample 201 prior to hardening of the epoxy. In addition, only the individual components may be disposed within the fluid flow lines 214, 216, thereby preventing a solidified mixture from existing in the flow lines 214, 216. Further, a small amount of a flush fluid and/or reaction kill agent can be used to displace any mixture from one or more of the fluid flow lines 214, 216 and/or the chamber 220 to prevent the epoxy from hardening within the fluid flow lines 214, 216 and/or the chamber 220.

The injector assembly 203 described herein may be configured to contact a plurality of fluids within the core holder 200, and/or introduce the mixed fluids to a core sample 201 within a desired distance and/or time of mixing. In an embodiment, a flow path between the chamber 220 and the core sample 201 may be less than about 3 inches, less than about 2 inches, less than about 1 inch, less than about 0.5 inches, less than about 0.4 inches, less than about 0.3 inches, less than about 0.2 inches, or less than about 0.1 inches. In an embodiment, the time between a fluid entering the chamber 220 and/or mixing with another fluid to the time when the mixed fluid contacts the core sample 201 may be controlled. The time may be less than about 60 seconds, less than about 10 seconds, less than about 5 seconds, less than about 4 seconds, less than about 3 seconds, less than about 2 seconds, or less than about 1 second.

The injector assembly 203 described herein may be used with any suitable core holder. In general, a suitable core holder is any apparatus configured to retain a rock or mineral sample and pass a fluid therethrough. In an embodiment, suitable core holders may include, but are not limited to, single axis core holders, biaxial core holders, and/or triaxial core holders. Single axial core holders may be referred to as Hassler type core holders in some embodiments and comprise core holders configured to provide a radial pressure applied to a core sample. As used herein, a "radial pressure" refers to a pressure applied on the core sample in a direction towards the longitudinal axis of the core sample and core holder. Biaxial core holders comprise core holders configured to provide a common radial and axial pressure applied to a core sample. As used herein, an "axial pressure" refers to a pressure applied to an end of the core sample in a direction aligned with the longitudinal axis of the core sample and core holder. Triaxial core holders comprise core holders configured to provide independent radial and axial pressures to the core sample. Each of these core holder types is described in more detail below.

Figure 5:
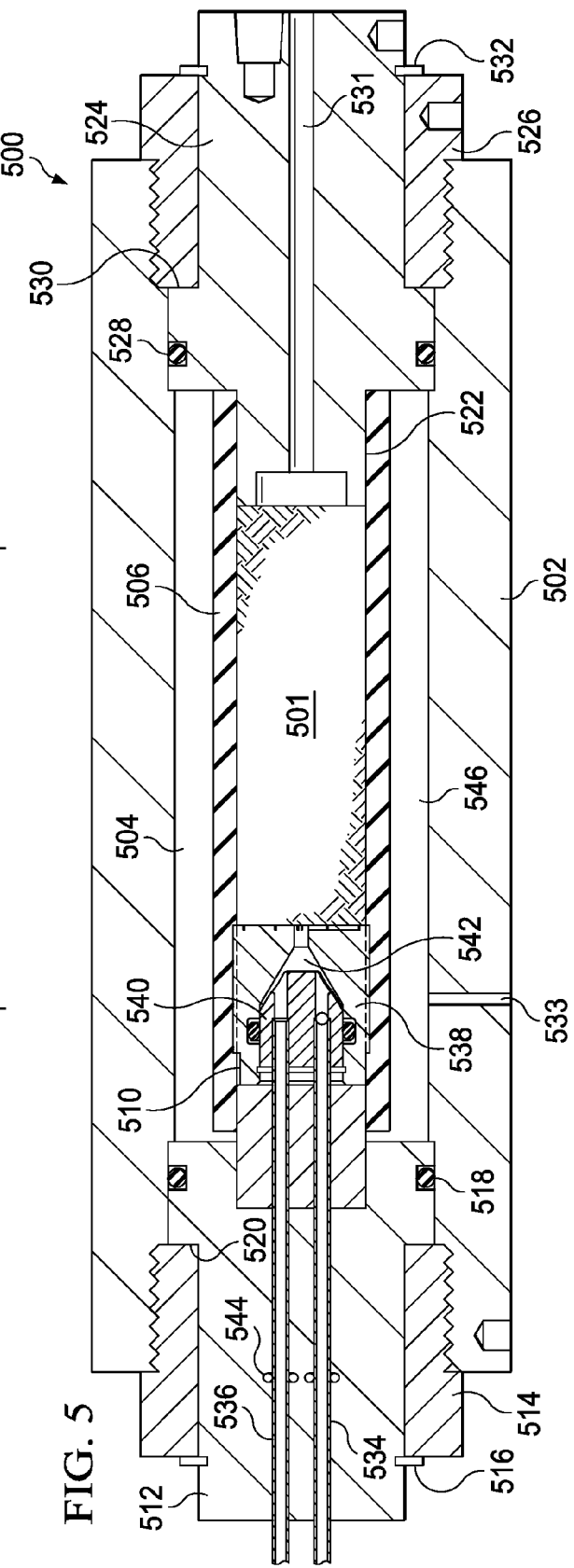
FIG. 5 illustrates a cross sectional view of a core holder according to another embodiment.

An embodiment of a single axis core holder 500 is shown in FIG. 5. The single axis core holder 500 is configured to provide a radial pressure to the core sample. The radial pressure may server several purposes. First, the radial pressure applied to the sleeve 506 may maintain an engagement between the sleeve 506 and the radial surface of the core sample 501 to prevent the channeling of fluid around the core sample 501 rather than through the core sample 501. Second, the radial pressure may allow the conditions in which the core sample 501 is expected to be exposed to a fluid to be modeled. For example, the radial pressure may be used to simulate an overburden pressure encountered within a wellbore. The sample properties under the simulated conditions can then be determined.

As shown in FIG. 5, a housing 502 comprises a central flow passage 504. The sleeve 506 can be disposed about a core sample 501 within the housing 502 and may be formed of a variety of materials such as a resilient material (e.g., an elastomer). A first end of the sleeve 506 is stretched over and engages the shoulder 510 of the first end cap 512 which is secured in a first end of the housing 502. In an embodiment, the first end cap 512 may be engaged with the housing 502 by a plug 514 having external threads that are threaded to the housing 502. A seal 518 (e.g., an elastomeric seal such as an o-ring) may be provided between first end cap 512 and the housing 502. The first end cap 512 may comprise a shoulder 520 that engages the plug 514 to retain the first end cap 514 within the housing 502. A retaining ring 516 may be disposed in a recess in the first end cap 512 to further retain the engagement between the first end cap 512 and the plug 514.

A second end of the sleeve 506 is stretched over and engages the shoulder 522 of the second end cap 524 which is secured in a second end of the housing 502. In an embodiment, the second end cap 524 may be engaged with the housing 502 by a plug 526 having external threads that are threaded to the housing 502. A seal 528 (e.g., an elastomeric seal such as an o-ring) may be provided between second end cap 524 and the housing 502. The second end cap 524 may comprise a shoulder 530 that engages the plug 526 to retain the second end cap 524 within the housing 502. A retaining ring 532 may be disposed in a recess in the second end cap 524 to further retain the engagement between the second end cap 524 and the plug 526. A fluid outlet 531 may be disposed within the second end cap 524 to provide a fluid communication pathway between the core sample 501 and an outlet of the core holder adjacent the second end cap 524.

The injector assembly as described herein may be disposed within the housing 502 and be fixed with respect to the first end cap 512. The injector assembly may be substantially similar to the injector assembly described above with respect to FIGS. 3A, 3B, and 3C, and may comprise a plurality of fluid flow lines 534, 536 engaged with a receiver 540. The receiver may be engaged within a body portion 538 to form the chamber 542. The plurality of fluid flow lines 534, 536 may inserted through the first end cap 512, and one or more seals 544 may be disposed within corresponding recesses within the first end cap 512 to provide a seal between the plurality of fluid flow lines 534, 536 and the first end cap 512.

During use, a fluid may be introduced into the annular region 546 through one or more ports 533. The fluid (e.g., a gas and/or a liquid) may apply a pressure against the outer surface of the sleeve 506, which may be applied to the core sample 501 by the sleeve 506. Any suitable pressure capable of being maintained within the housing 502 may be applied to the sleeve 506, and thereby, to the core sample 501. One or more fluids may then be introduced into the fluid flow lines 534, 536 where they may be contacted and mixed in the chamber 542 before being introduced to the core sample 501. The pressure of the fluid or fluids introduced into the core sample 501 will generally be less than the pressure applied to the outside of the sleeve 506 to avoid expanding the sleeve 506. One or more properties of the core sample 501 may then be determined through performing one or more tests and measuring one or more properties of the fluid and/or core sample.

The core sample 501 may be removed by removing the plug 526 and then the second end cap 524 to allow for access to the core sample 501. The pressure may be reduced in the annular area 546 to aid in separating the sleeve from the core sample 501. Alternatively or in addition to removing the second end cap 524, the plug 514 may be removed and the first end cap 512 may be removed to allow for access to the core sample 501 from the first end. Another core sample can then be inserted into the sleeve and the core holder can be reassembled. The pressure in the annular region 546 can then be established and the core sample can be tested as desired.

Returning to FIG. 2B, an embodiment of a biaxial core holder 200 is shown. The biaxial core holder 200 is configured to provide a common radial and axial pressure to a core sample. As noted with respect to the core holder 500, the radial pressure applied to the sleeve 206 may maintain an engagement between the sleeve 206 and the radial surface of the core sample 201 to prevent the channeling of fluid around the core sample 201 rather than through the core sample 201. The common radial pressure and axial pressure may allow the conditions in which the core sample 201 is expected to be exposed to a fluid to be modeled. For example, the common radial and axial pressure may be used to simulate an overburden and pore pressure on a rock sample within a subterranean formation.

As shown in FIG. 2B, several of the components are similar to the components illustrated in FIG. 5, and the common components will not be discussed in detail in the interest of clarity. For example, the first end cap 212 and the second end cap 224 may be engaged with the housing 202 as described above with respect to FIG. 5. In this embodiment, the injector assembly may be configured to move independently from the first end cap 212. A first end of the sleeve 206 is stretched over and engages the shoulder 210 of the injector assembly. The injector assembly may be similar to the injector assembly described above with respect to FIGS. 3A, 3B, and 3C, and may comprise a plurality of fluid flow lines 214, 216 engaged with a receiver 208. The receiver 208 may be engaged within a body portion 218 to form the chamber 220. The plurality of fluid flow lines 214, 216 may inserted through the first end cap 212, and one or more seals 222 may be disposed within corresponding recesses within the first end cap 212. The seals 222 may provide a sealing engagement between the fluid flow lines 214, 216 and the first end cap 212 if and/or when the fluid flow lines 214, 216 move due to a movement of the injector assembly.

During use, a fluid may be introduced into the annular region 226 through one or more ports 232. The fluid (e.g., a gas and/or a liquid) may apply a pressure against the outer surface of the sleeve 206, which may be applied to the core sample 201 by the sleeve 206. The fluid may also apply a pressure against a surface 228 of the injector assembly, thereby applying a common pressure to both the radial surface of the core sample 201 through the sleeve 206 and the axial surface of the core sample 201 through the injector assembly. Any suitable pressure capable of being maintained within the housing 202 may be applied to the sleeve 206, and thereby, to the core sample 201. One or more fluids may then be introduced into the fluid flow lines 214, 216 where they may be contacted and mixed in the chamber 220 before being introduced to the core sample 201. The pressure of the fluid or fluids introduced into the core sample 201 will generally be less than the pressure applied to the outside of the sleeve 206 to avoid expanding the sleeve 206. One or more properties of the core sample 201 may then be determined through performing one or more tests and measuring one or more properties of the fluid and/or core sample. The core sample 201 may be removed in the same way as described above with respect to FIG. 5.

Figure 6:
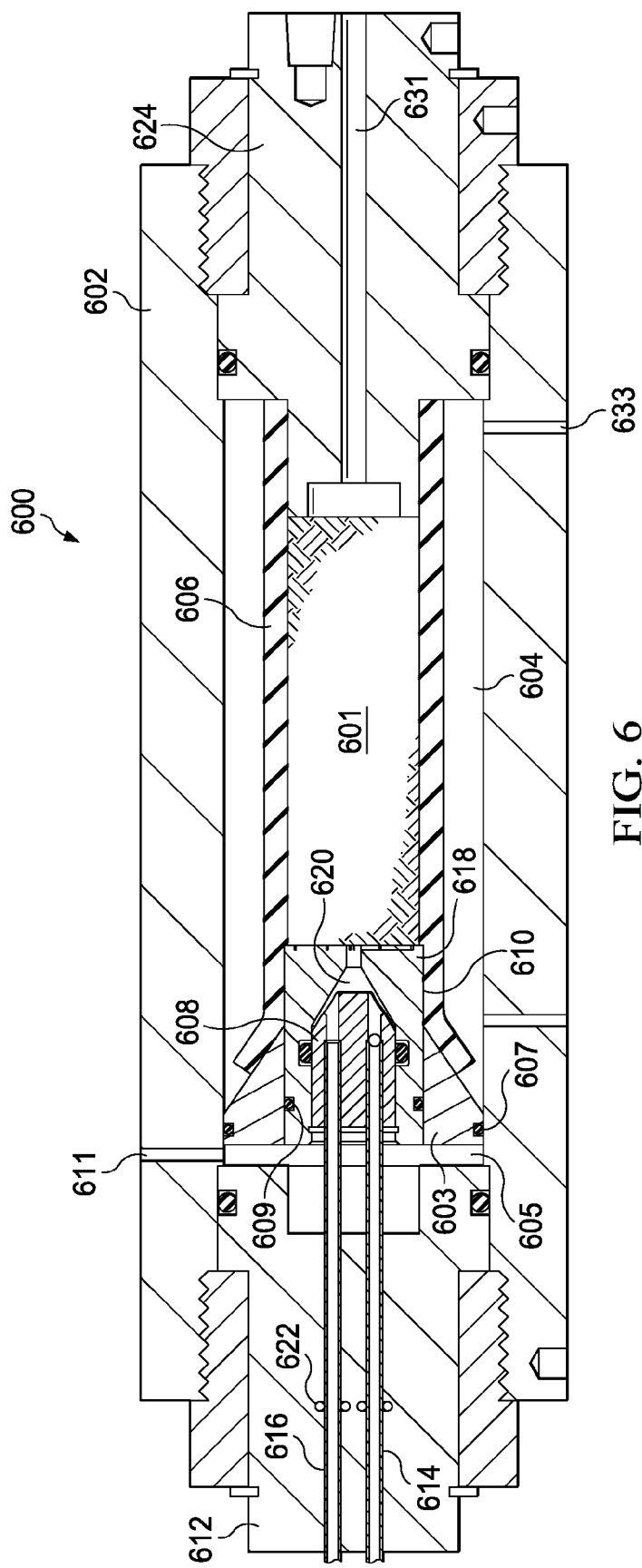
FIG. 6 illustrates a cross sectional view of a core holder according to still another embodiment.

An embodiment of a triaxial core holder 600 is illustrated in FIG. 6. The triaxial core holder 600 is configured to provide an independent radial and axial pressure to a core sample. As noted with respect to the core holder 500, the radial pressure applied to the sleeve 606 may maintain an engagement between the sleeve 606 and the radial surface of the core sample 601 to prevent the channeling of fluid around the core sample 601 rather than through the core sample 601. The independent radial pressure and axial pressure may allow the conditions in which the core sample 601 is expected to be exposed to a fluid to be modeled. For example, the radial pressure may be used to simulate an overburden pressure on a sample within a subterranean formation, while the axial pressure may be different than the radial pressure and used to simulate an expected wellbore pressure in contact with the core sample. In this case, the expected axial and radial pressures may be different based on the simulated orientation and location of the core sample within the subterranean formation.

As shown in FIG. 6, several of the components are similar to the components illustrated in FIG. 5, and the common components will not be discussed in detail in the interest of clarity. For example, the first end cap 612 and the second end cap 624 may be engaged with the housing 602 as described above with respect to FIG. 5. In this embodiment, the injector assembly and the first end cap 612 may be configured to move independently. A first end of the sleeve 606 is stretched over and engages the shoulder 610 of the injector assembly. The injector assembly may be similar to the injector assembly described above with respect to FIGS. 3A, 3B, and 3C, and may comprise a plurality of fluid flow lines 614, 616 engaged with the receiver 608. The receiver 608 may be engaged within a body portion 618 to form the chamber 620. The plurality of fluid flow lines 614, 616 may inserted through the first end cap 612, and one or more seals 622 may be disposed within corresponding recesses within the first end cap 612. The seals 622 may provide a sealing engagement between the fluid flow lines 614, 616 and the first end cap 612 if the fluid flow lines 614, 616 move due to a movement of the injector assembly.

A mandrel 603 may engage the injector assembly and provide for a fluid chamber 605 disposed between the housing 602, a surface of the mandrel 603 and/or the injector assembly, and a surface of the first end cap 612. The mandrel 603 may have one or more seals 607 disposed in a corresponding recess to provide a sealing engagement between the mandrel 603 and the housing 602. One or more seals 609 may also be disposed in a corresponding recess between the mandrel 603 and the body portion 618 to provide a sealing engagement between the mandrel 603 and the body portion 618. The mandrel may be configured to provide a moveable, but fluid tight connection between the chamber 605 and the annular region 604.

During use, a fluid may be introduced into the annular region 604 through one or more ports 633. The fluid (e.g., a gas and/or a liquid) may apply a pressure against the outer surface of the sleeve 606, which may be applied to the core sample 601 by the sleeve 606. A separate fluid may also be introduced into the chamber 605 through one or more ports 611. The fluid may apply pressure against the surface of the mandrel 603 and/or the injector assembly, which may be applied to the surface of the core sample 601. Thus the fluid pressure applied against the mandrel 603 and/or the injector assembly by the fluid in the chamber 605 is independent of fluid pressure which is applied to the radial surface of the sleeve 606. This configuration may allow the axial load on the core sample 601 to be varied without changing or modifying any force which may be applied radially on the core sample 601 through the sleeve 606. Similarly, the radial force applied through sleeve 606 on the core sample 601 may be varied without changing the axial force applied on the core sample 601. Alternately, both the radial force and the axial force applied on the core sample 601 may be varied. The ability to change the radial and axial pressure independently may be useful for some tests performed on the core sample 601.

One or more fluids may then be introduced into the fluid flow lines 614, 616 where they may be contacted and mixed in the chamber 620 before being introduced to the core sample 601. A fluid outlet 631 is provided for allowing fluids passing through the core to be removed, though in some embodiments, the fluid outlet 631 may be used to introduce fluids into the core sample 601. The pressures of the fluid or fluids introduced into the core sample 601 will generally be less than the pressure applied to the outside of the sleeve 606 to avoid expanding the sleeve 606. One or more properties of the core sample 601 may then be determined through performing one or more tests and measuring one or more properties of the fluid and/or core sample. The core sample 601 may be removed in the same way as described above with respect to FIG. 5.

The injector assembly described herein may be used to provide a variety of fluids to a core holder and combine the fluids within the core holder. The configuration of the injector assembly may allow for a single fluid provided through a single fluid flow line to be introduced to the core sample. Alternatively, two or more fluids may be provided through two or more of the fluid flow lines for mixing within the injector assembly. Suitable fluids may comprise various multi-component fluids used within a subterranean formation for a variety of drilling, drill-in, completion, workover, and/or abandonment operations throughout the life of a wellbore. For example, various fluids that can be used to test a core sample may include, but are not limited to, aqueous and/or hydrocarbon based fluids comprising emulsifiers, viscosifiers, emulsion destabilizers, antifreeze agents, biocides, algaecides, pH control additives, oxygen scavengers, clay stabilizers, weighting agents, degradable fluid loss agents, foaming agents, foaming fluids (e.g., gases), consolidating agents, and the like. In an embodiment, two fluids that react to form a reaction product may be used with the injector assembly described herein. For example, various multi-component fluids such as a multicomponent resin and/or an epoxy useful as consolidating agent may be introduced into the chamber via separate fluid flow lines and mixed prior to contacting the core sample.

Various tests can be performed using the core holders described herein. In an embodiment, the various measurements of the core sample and/or the fluid passing through the core sample may be used to determine one or more properties of the fluid and/or the core sample such as the permeability, regained permeability, porosity, fluid flow, fluid saturation and/or gas saturation in the core sample. As an example, a regained permeability test may be performed using a core holder and a sample core disposed therein. A regained permeability test generally comprises using a core sample indicative of the formation of interest. The core sample may be saturated in an aqueous fluid such as a filtered API brine. The core sample may then be mounted in the core holder as described above. A fluid pressure may be applied outside the sleeve to provide an overburden pressure on the core sample within the sleeve. The core sample may be heated to and then maintained at a desired temperature throughout the test. The core is then flushed with a fluid in a modeled production direction. An initial permeability may be determined in the production direction by measuring the flow through the core sample at a given pressure. A test fluid may then be introduced through the injector assembly in an injection direction, that may be defined as being opposite the initial production direction. In an embodiment, a multi-component fluid may be introduced through two or more fluid flow lines and mixed in the chamber of the injector assembly. For example, a two component epoxy may be injected through two fluid flow lines, mixed in the chamber within the injector assembly, and thereafter introduced into the core sample. The epoxy may be used as a consolidating agent useful in forming gravel and/or sand packs, for example. After introducing the test fluid, the core sample may be left to equilibrate for a representative amount of time. A fluid may then be introduced to the core sample in the production direction and a regained permeability may then be measured based on the pressure and flow rate through the core sample. Similar processes may be performed for various types of fluids used in a wellbore environment.

The results of one or more tests may be used to determine a fluid composition for use in a wellbore. As described above with respect to FIG. 1, a wellbore may be formed in a subterranean formation and a sample of the subterranean formation may be obtained. The sample may comprise a core sample and/or the sample may be used to determine a representative property of the formation for identifying a similar rock sample to be used as a core sample. The core sample may then be tested using a core holder as described herein to obtain one or more properties of the core sample. Based on these test results, a fluid for use with the subterranean formation may be selected. For example, if a regained permeability test for a first consolidating agent results in a measured regained permeability beyond a threshold, a second consolidating agent may be tested using another core sample. If the second consolidating agent results in a measured regained permeability that meets and/or falls within the threshold, then the second consolidating agent may be selected for use with the subterranean formation. In the same way, the use of the core holder may be used to test and select one or more fluids for use with the wellbore disposed in the subterranean formation throughout the life of the wellbore.

While the core holder described herein is generally described with respect to a core sample obtained from and/or representative of a subterranean formation, the core holder may also be used with rock samples from other locations and/or for use with other industries. For example, obtaining one or more properties of one or more rock samples using the core holder described herein may be useful in various geological surveying, mining, and/or construction related fields. The use of the core holder comprising the injector assembly described herein can also be used to test rock samples in any of these industries.

Having been described, it can be seen that the core holder allows for a plurality of fluids to be introduced in proximity of the core itself before being mixed in a chamber within a housing of the core holder. This configuration may allow the time that a multicomponent fluid is mixed prior to being introduced to the core sample to be reduced relative a core holder having a single fluid flow line. This configuration may also prevent a fluid used with the core holder from reacting in an fluid flow line and clogging the line during a test procedure. In addition, one or more features may be disposed in the mixing chamber to allow for improved comingling of the fluids prior to being introduced to the core sample. One or more check valves may be used with the fluid flow lines to help prevent backflow of fluid if less than the total number of fluid flow lines are used. The use of the plurality of fluid flow lines may be used with a single axis, biaxial, and/or triaxial core holder.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present invention.

What is claimed is:

1. A core holder comprising:
   a plurality of fluid flow lines;

a housing;

a core sleeve disposed within the housing;

an end cap coupled to a first end of the core sleeve and a first end of the housing; and an injector assembly disposed within the housing and coupled to a second end of the core sleeve, wherein the injector assembly comprises:

a plurality of fluid passages coupled to the plurality of fluid flow lines;

a receiver comprising the plurality of fluid passages and a body portion; and a chamber in fluid communication with the plurality of fluid passages and an interior of the sleeve, wherein the chamber is defined by a surface of the receiver and a surface of the body portion.

2. The core holder of claim 1, further comprising an annular region defined between an inner surface of the housing and an outer surface of the core sleeve, wherein the annular region is configured to accept a pressurized fluid.

3. The core holder of claim 1, wherein the injector assembly further comprises a distributor disposed on an end of the injector assembly within the core sleeve.

4. The core holder of claim 1, wherein the core holder comprises a single axis core holder, a biaxial core holder, or a triaxial core holder.

5. The core holder of claim 1, further comprising a second end cap coupled to a second end of the housing.

6. The core holder of claim 5, wherein a ratio of a first distance between an outer surface of the second end cap and the chamber and a second distance between the chamber and an adjacent surface of a core sample disposed within the core sleeve is in the range of about 1:20 to about 20:1.

7. The core holder of claim 1, wherein the chamber comprises one or more mixing features.

8. The core holder of claim 7, wherein the one or more mixing features comprise one or more surface features disposed on an inner surface of the chamber, one or more fins disposed within the chamber, a mesh fill within the chamber, a gauze fill within the chamber, one or more mixing members disposed within the chamber, or any combination thereof.

9. The core holder of claim 1, further comprising a check valve disposed in one or more of the plurality of flow passages.

10. The core holder of claim 9, wherein the one or more of the plurality of flow passages comprise a seat, and wherein the check-valve comprises a ball disposed within the one or more of the plurality of flow passages.

11. A core holder comprising:

a housing; and an injector assembly disposed within the housing and coupled to a core sleeve disposed within the housing, wherein the injector assembly is configured to:

receive a plurality of fluids through a plurality of fluid flow lines;

contact the plurality of fluids to form a combined fluid; and provide a fluid pathway out of the injector assembly for the combined fluid to pass to the interior of the core sleeve, wherein the injector assembly comprises a chamber in which the plurality of fluids contact to form the combined fluid.

12. The core holder of claim 11, wherein the injector assembly further comprises:

a body portion;

a receiver configured to receive the plurality of fluid through the plurality of fluid flow lines, wherein the chamber is defined by a surface of the receiver and a surface of the body portion; and the fluid pathway, wherein the fluid pathway is in fluid communication with the chamber and the interior of the core sleeve.

13. The core holder of claim 11, wherein the injector assembly is further configured to generate a turbulent flow upon contacting the plurality of fluids to improve the mixing and form the combined fluid.

14. The core holder of claim 11, further comprising one or more flow valves coupled to one or more of the plurality of fluid flow lines, wherein the flow valves are configured to impede flow through the one or more of the plurality of fluid flow lines in a first direction and allow flow through the one or more of the plurality of fluid flow lines in a second direction.

15. The core holder of claim 11, wherein the injector assembly is further configured to provide the combined fluid to a core sample disposed within the core sleeve within a controlled time of the plurality of fluids being contacted to form the combined fluid.

16. A method of testing a core sample comprising:

receiving a plurality of fluids within a core holder;

combining the plurality of fluids within a chamber within the core holder to form a combined fluid;

passing the combined fluid from the chamber through a fluid pathway;

contacting the combined fluid with a core sample within the core holder after passing the fluid through the fluid pathway; and determining one or more properties of the core sample.

17. The method of claim 16, wherein the one or more properties of the core sample comprise a permeability, a regained permeability, a porosity, a fluid flow through the core sample, a fluid saturation in the core sample, a gas saturation in the core sample, or any combination thereof.

18. The method of claim 16, wherein the plurality of fluids react to form a reaction product in the combined fluid.

19. The method of claim 16, further comprising selecting a fluid for use in a subterranean formation based on the one or more properties of the core sample.

* * * * *